United States Patent
Triglia et al.

(10) Patent No.: US 8,715,954 B2
(45) Date of Patent: May 6, 2014

(54) METHOD OF PRODUCING C3A SERUM-FREE CLONAL CELL LINE

(75) Inventors: Dennis Triglia, San Diego, CA (US); Anthony Purchio, Solana Beach, CA (US)

(73) Assignee: Vital Therapies, Inc., San Diego, CA (US)

( * ) Notice: Subject to any disclaimer, the term of this patent is extended or adjusted under 35 U.S.C. 154(b) by 466 days.

(21) Appl. No.: 12/143,631

(22) Filed: Jun. 20, 2008

(65) Prior Publication Data

US 2009/0035805 A1    Feb. 5, 2009

Related U.S. Application Data

(60) Division of application No. 10/723,590, filed on Nov. 25, 2003, now Pat. No. 7,390,651, which is a continuation of application No. 09/022,469, filed on Feb. 11, 1998, now Pat. No. 6,653,105.

(51) Int. Cl.
    *C12P 21/02* (2006.01)

(52) U.S. Cl.
    USPC .............................. 435/29; 435/370; 435/70.3

(58) Field of Classification Search
    None
    See application file for complete search history.

(56) References Cited

U.S. PATENT DOCUMENTS

| | | | |
|---|---|---|---|
| 4,675,002 A | 6/1987 | Viles et al. | |
| 4,853,324 A | 8/1989 | Viles et al. | |
| 5,290,684 A | 3/1994 | Kelly | |
| 5,480,825 A * | 1/1996 | Gazitt | 435/372.3 |
| 5,529,920 A | 6/1996 | Cole et al. | |
| 5,595,909 A | 1/1997 | Hu et al. | |
| 5,605,835 A | 2/1997 | Hu et al. | |
| 5,804,441 A | 9/1998 | Nagamori et al. | |
| 5,869,243 A | 2/1999 | Jauregui et al. | |
| 6,103,529 A | 8/2000 | Price et al. | |

FOREIGN PATENT DOCUMENTS

| | | |
|---|---|---|
| WO | WO 91/18087 A1 | 11/1991 |
| WO | WO 98/08935 A1 | 3/1998 |

OTHER PUBLICATIONS

Strain et al., "A bioartificial liver—state of the art", *Science*, vol. 295, p. 1005-1009 (2002).

Spiering et al., "Properties of the hepatix C3A human hepatoblastoma cells cultured in a hollow fiber bioreactor", In Vitro *Cellular and Developmental Biology Animal*, vol. 30A, No. 3, Part 2, pp. 106 (1994).

Jayme et al., Culture Media for Propagation of Mammalian Cells, Viruses, and Other Biologicals, *Advances in Biotechnological Processes*, 5:1-30 (1985).

\* cited by examiner

*Primary Examiner* — Sharon Wen
(74) *Attorney, Agent, or Firm* — DLA Piper LLP (US)

(57) ABSTRACT

A serum-free C3A clonal cell line and methods for generating the same are provided. The C3A cell line has a reduced doubling time in serum-free medium compared to a corresponding C3A cell line from which it is derived. Methods using the cells of the serum-free C3A clonal cell line for the production, expression and recovery of harvestable polypeptides, screening compounds for metabolic activity, studying enteric disease and for use in a bio-artificial liver device are also provided.

7 Claims, 2 Drawing Sheets

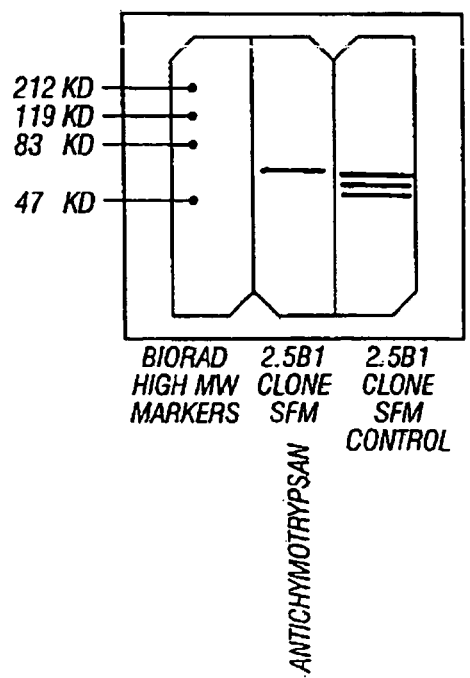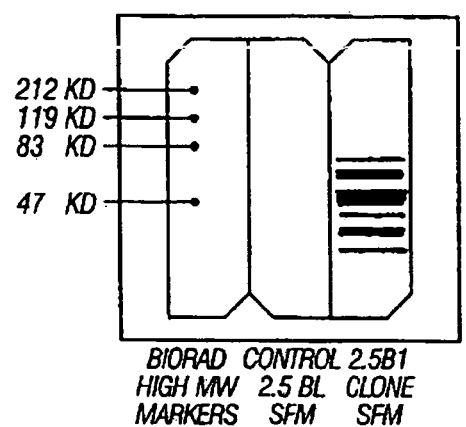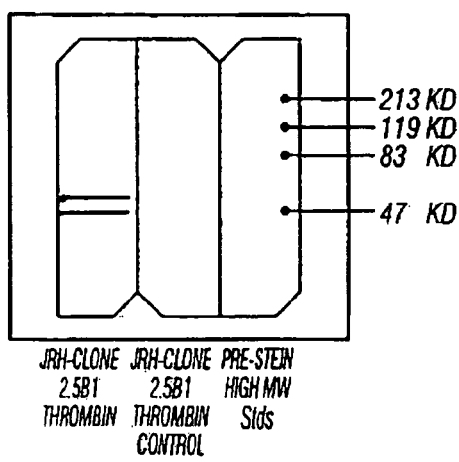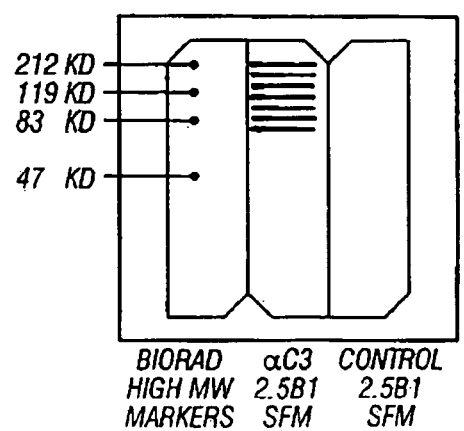

METHOD OF PRODUCING C3A SERUM-FREE CLONAL CELL LINE

CROSS REFERENCE TO RELATED APPLICATIONS

This application is a divisional application of U.S. application Ser. No. 10/723,590 filed Nov. 25, 2003, now issued as U.S. Pat. No. 7,390,651; which is a continuation application of U.S. application Ser. No. 09/022,469 filed Feb. 11, 1998, now issued as U.S. Pat. No. 6,653,105. The disclosure of each of the prior applications is considered part of and is incorporated by reference in the disclosure of this application.

BACKGROUND OF THE INVENTION

1. Field of the Invention

This invention relates generally to the field of cell lines, more specifically to a serum-free C3A cell line that produces mammalian cell products, such as harvestable polypeptides obtained by recombinant methods.

2. Background Information

Cell culture is widely used for the production of various harvestable bio-products including polypeptide growth factors, hormones, enzymes, vaccines and proteins. These bio-products are produced in culture by normal, transformed and genetically engineered cell lines.

When a cell is removed from its native environs, however, an artificial medium must provide all the critical factors necessary for normal cell growth, differentiation and host cell expression. Thus, the synthetic culture medium must supply critical nutritional, hormonal, and stromal factors normally provided in vivo. Furthermore, the culture medium should not interfere with the production or use of the desired bio-product. Since the function of many cell culture factors remain undefined at the molecular level, most cell lines used in the production of biologicals are grown in culture medium supplemented with animal serum which serves as a universal nutrient. Serum is a very complex fluid, containing at least 500 different protein components including hormones, growth factors, carrier proteins, trace elements and attachment and spreading factors among other constituents. Animal serum, such as fetal bovine serum (FBS), can represent up to 10% of a typical culture medium. Currently, C3A cells are grown in tissue culture medium containing approximately 5% FBS.

Although widely employed, serum supplementation has many limitations, particularly when utilized in the manufacture of biotechnology products (Barnes, 3987; Barnes & Sato 1980; Broad, i.e., 1991; Jayme, 1991). Serum contains high levels of numerous proteins that can interfere with heterologously expressed polypeptides and it must subsequently be separated from manufactured bio-products during their harvest. Additionally, the increasing rise in the price of commercial serum, the uncontrollable variation in its batch quality and the additional requirement for its sterilization, combine to complicate the production process and to inflate manufacturing costs.

Furthermore, serum use may present a potential bio-hazard. Serum can contain cryptic cytotoxic elements that must be removed before any biological product can be safely utilized after manufacture. Serious regulatory apprehension has been voiced by the United States Food and Drug Administration concerning the possible contamination of harvestable bio-products from cultures containing serum. Rossi, et al, (*Am J. Vet. Res.,* 41:1680-1681 (1980)); Chu, et al., (*In vitro,* 9:31-34 (1973)); and Nuttall, et al, (*Nature,* 266:835-837 (1977))) address one aspect of this problem (viz., the potential for viral contamination of serum containing cell cultures). Viral contaminants may interact biologically with mammalian cells in culture, as noted by Chu, et al., or through obscure clinical reactions to other agents, as observed by Nuttall, et al.

A number of techniques have been employed to alleviate viral contamination of serum containing cultures. These include vigilant screening and eradication of contaminating viruses by affinity chromatography. Unfortunately, however, as reported by Orr et al, [*J. Cain. Microbial.,* 3:402-5 (1976)), it is difficult to assure complete elimination of all possible undesirable agents that may exist in a contaminated cell culture. Recently, additional concerns have arisen concerning adulteration by agents of non-viral origin. Such fears have subsequently been confirmed by evidence of the transmission of prion-type diseases from animals to humans (e.g., neurodegenerative disorders such as Creutzfeldt-Jakob and most recently by a human form of Bovine Spongioform Encephalopathy; Collinge, *J., Hum. Mol. Genet.* 6: 1699-1705; 1997). These developments have raised further serious concerns over the use of animal-derived sera in cell culture.

Consequently, there is a high demand for the development of cell lines that are adapted for growth and culture in medium that is free of serum. Galfre, U.S. Pat. No. 4,350,683 describes a rat myeloma cell line (CNCM 1-078), useful in the development of rat-rat hybridomas. that is allegedly capable of growth in a serum-free medium. In many serum-free cultures, however, cell growth is often reported to be slower compared to cell growth in cultures supplemented with serum. Golde, U.S. Pat. No. 4,438,032 describes a human T-lymphoblast cell line (Mo) capable of growth in serum-free medium, although its rate of growth is considerably slower than when the cells are grown and maintained in medium containing 20% FBS. Furthermore, serum-free cell lines have also been reported to suffer from diminished cell density, decreased saturation levels, and reduced viability.

Consequently, there is a need to create serum-free cell lines that can grow and flourish when maintained in serum-free medium (including "chemically-defined" medium that is free of any type of serum or serum supplement), Such serum-free cell lines should also exhibit normal viability, rates of growth and be capable of expressing harvestable bio-products that are free of biological contamination.

Accordingly, the present invention offers a cell line—clonally derived from a parental C3A hepatocyte cell line—that is adapted for normal growth and maintenance in serum-free medium. Additionally, the present cell line supports the synthesis and expression, in serum-free culture, of substantial titers of harvestable bio-products at reasonably high purity including polypeptides and proteins. One advantage of the serum-free C3A cell line of the invention is that bio-products harvested from cultures utilizing these cells have considerably less risk of harboring cryptic infectious agents than bio-products manufactured with supplements containing serum. Another advantage is the likely facilitation of regulatory approval for bio-products derived using cells of the invention due to their reduced risk of contamination. One regulatory agency, the United States Department of Agriculture, is particularly concerned about the inadvertent introduction of Hoof and Mouth disease into United States livestock through importation of contaminated bio-products produced from cultures containing fetal calf serum. Consequently, the cell line of the invention and methods of its use offer advantages over cell lines that are grown or maintained in serum-containing medium.

SUMMARY OF THE INVENTION

The present invention is based on the discovery and development of a serum-free cell line derived from a parental hepatocyte C3A cell line. The serum-free C3A cell line is adapted for growth and cloned in serum-free medium. A surprising advantage of the serum-free C3A cells is that they have a higher growth rate and shorter doubling time than cells of the parental C3A line. The C3A serum-free cell line supports the production of harvestable bio-products in serum-free culture thereby diminishing the risk of producing contaminated bio-products through serum transmission.

In a first aspect, the serum-free C3A cell line of the present invention has a doubling time significantly shorter than the doubling time of the parental or a comparable C3A cell line.

In another aspect, cells of the serum-free C3A cell line express a single or any combination of a plurality of harvestable bio-products in serum-free cell culture.

In yet a further aspect, the harvestable bio-products produced using the serum-free C3A cells are mammalian polypeptides such as alpha fetal protein (AFP), human albumin. α-1-antichymotrypsin, α-1-antitrypsin, antithrombin III, complement C3, Factor V and transferrin.

In another aspect of the invention, a method is provided for producing a serum-free C3A cell line and a method for producing harvestable bio-products by employing cells of the C3A serum-free cell line.

In another aspect of the invention, a method and a device is provided for treating a subject suspected of having a liver disorder, condition, or compromised liver function by employing cells of the serum-free C3A cell line in a bio-artificial liver device.

In another aspect of the invention, a method is provided for screening compounds for metabolic activity or for studying enteric disease using cells of the serum-free C3A cell line.

BRIEF DESCRIPTION OF THE DRAWINGS

The following drawings are illustrative of embodiments of the invention and are not meant to limit the scope of the invention as encompassed by the claims.

FIGS. 1A through 1F are illustrations showing the results of Western Blots using 10% SDS-PAGE gels for detection of harvestable polypeptides expressed from cells of the serum-free C3A cell line cultured in serum-free medium.

FIG. 1A demonstrates the detection of the harvestable bio-product α-1-antichymotrypsin.

FIG. 1B demonstrates the detection of the harvestable bio-product α-1-antitrypsin.

FIG. 1C demonstrates the detection of the harvestable bio-product antithrombin III.

FIG. 1D demonstrates the detection of the harvestable bio-product complement C3.

FIG. 1E demonstrates the detection of the harvestable bio-product Factor V.

FIG. 1F demonstrates the detection of the harvestable bio-product transferrin.

DETAILED DESCRIPTION OF THE INVENTION

Figure 1E:
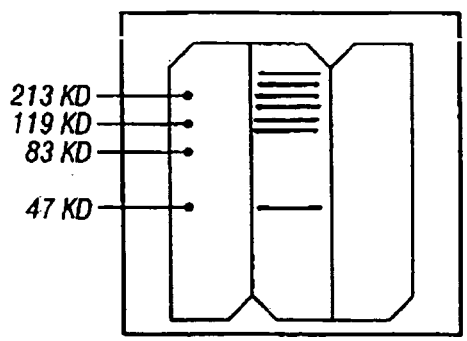

The present invention provides a serum-free C3A hepatocyte cell line suitable for use in the production of harvestable bio-products in serum-free culture. The serum-free C3A cell lines of the present invention are derived from a known parental C3A cell line. The term "derived," as used herein means that the cell line is cloned from a known parental C3A cell line by a defined selection method provided herein. The term "cloned," "clonally derived" or "clonal cell line" as used herein means a propagating population of genetically identical cells from a specific cell line that are derived from a single progenitor cell. The parental cell line is a liver cell line similar to the cell line described in U.S. Pat. No. 5,290,684. The clonally derived serum-free C3A cell line of the invention retains most of the characteristics of the human hepatocyte parent C3A line with the exception that the presently claimed cell line is grown, maintained and expresses liver-specific biological activity in medium that is free of serum. The serum-free cell line of the invention and methods of its use mimic both qualitatively and quantitatively liver cells or the liver as functioning organ. Serum-free C3A cells express near normal levels of polypeptides from several central metabolic pathways, including pathways for glycolysis, gluconeogenesis, glycogenesis and ureogenesis. In addition, the serum-free cells include the following additional characteristics: they synthesize near normal levels of albumin and other proteins, they contain high levels of liver specific transcription factors, and they exhibit the structure and polarity characteristic of normal human hepatocytes.

It is to be understood that this invention is not limited to the particular methods, compositions and cell lines described herein, as such methods, compositions and cell lines may, of course, vary. It is also to be understood that the terminology used herein is for the purpose of describing particular embodiments only, and is not intended to limit the scope of the present invention which is only limited by the appended claims.

As used herein, including the appended claims, singular forms of words such as "a," "an." and "the" include their corresponding plural referents unless the context clearly dictates otherwise. Thus, for example, reference to "an organism" includes one or more different organisms, reference to "a cell" includes one or more of such cells, and reference to "a method" include reference to equivalent steps and methods known to a person of ordinary skill in the art, and so forth.

Unless otherwise defined, all technical and scientific terms used herein have the same meaning as commonly understood by a person of ordinary skill in the art to which this invention belongs. Although methods and materials similar or equivalent to those described herein can be used in the practice or testing of the present invention, suitable methods and materials are described below. All publications, patent applications, patents, and other references discussed above are provided solely for their disclosure prior to the filing date of the present application, Nothing herein is to be construed as an admission that the invention is not entitled to antedate any such disclosure by virtue of its prior invention. All publications, patent applications, patents, and other references mentioned herein are incorporated by reference in their entirety including all figures and drawings.

As used herein, the term "serum-free" means a culture medium formulated in the absence of serum, and its meaning includes both the media formulations, defined as "serum-free" media (which may otherwise be protein supplemented), "protein-free" media, (no protein supplementation) and "chemically defined" (ultra-pure with or without small molecular constituents, genetically engineered peptides or proteins). The proportions of the components of the serum-free medium can be adjusted and optimized for the particular use for which the cell line of the invention will be utilized, including its use in any particular polypeptide expression system, its use in a bio-artificial liver device, or its use in metabolic or enteric studies involving liver organ or hepatocyte cell function. To enhance the cell cultivation properties of serum-free medium used with cells of the invention, in addition to additives, the serum-free medium may also be supplemented with other components such as a fatty acids, amino acids, or phospholipid precursors. Serum-free medium can be purchased commercially or created de novo in the laboratory. Preferably, medium used with cells of the invention is serum-free and more preferably, it is supplemented with 2 mM L-glutamine. Even more preferably, the serum-free medium is the commercially obtainable variety designated as JRH Bioscience ExCell 620 that is supplemented with 2 mM L-glutamine.

The parental C3A cell line from which the cells of the invention are clonally derived is described in Gislason et al., *Artificial Organs* Vol. 18, pp. 385-38 (1994); Miwa et al., *Int. Jour, of Artificial Organs*, Vol. 19, pp. 240-244 (1996) and Sussman et al., *Hepatology*, Vol. 16, pp 60-65 (1992). It has been deposited with the American Type Culture Collection (ATCC), 1301 Parklawn Drive, Rockville, Md.? USA under ATCC Accession Number No. SD 2078 and No. SD 3283. The clonally derived serum-free C3A cells of the invention are also deposited with the ATCC and have Accession No. CRL-12461. The serum-free C3A cell line is free of biological contaminants and does not contain any hepatitis B virus (HBV) genetic sequences.

ATCC deposits are made under the provisions of the Budapest Treaty on the International Recognition of the Deposit of Microorganisms for the Purpose of Patent Procedure and the Regulations thereunder (Budapest Treaty). The treaty assures maintenance of viable cultures for 30 years from the date of deposit. The serum-free C3A cell line is available from the ATCC under the terms of the Budapest Treaty which assure permanent and unrestricted availability of progeny of the cell line to the public upon issuance of the pertinent U.S. patent or upon laying open to the public of any U.S. or foreign patent application, whichever comes first. The Budapest Treaty assures the availability of the cell line to one determined by the U.S. Commissioner of Patents and Trademarks to be entitled thereto according to 35 U.S.C. §122 and the Commissioner's rules pursuant thereto (including 37 CFR §1.14 with particular reference to 886 OG 638).

The assignee of the present application has agreed that if the cell line deposit should die. be lost or destroyed when cultivated under suitable conditions, it will be promptly replaced with a viable specimen of the same cell line upon proper notification. Availability of a deposited cell line is not to be construed as a license to practice the invention in contravention of the rights granted under the authority of any government in accordance with its patent laws.

Clones of serum-free C3A cells are capable of indefinite maintenance, growth, and proliferation in vitro. Continuous serum-free C3A cell lines proliferate, can be subcultured (i.e., passaged repeatedly into new culture vessels), and cryo-preserved over time (e.g., stored in the vapor phase of liquid nitrogen with a cryo-preservative such as 10% dimethylsulfoxide or glycerol). Serum-free C3A cells can be maintained in long-term culture as a cell line closely resembling primary cultures.

For the most part, cells of the invention are grown in any vessel, flask, tissue culture dish or device used for culturing cells that provides a suitable surface for cell attachment and spreading (e.g., Culture of Hematopoietic Cells (Culture of Specialized Cells) R. I. Freshney et al., Ed., I. Freshney; Wiley-Liss 1994; incorporated by reference herein). Typically, a foundative culture, is one in which cells are removed from an existing parental C3A stock, placed in a culture vessel in a mixture of serum containing and serum-free medium, and subsequently passaged to serum-free status as described in detail herein.

As used herein, the term "attachment" refers to cell adherence and spreading on a surface in such a device, where factors promoting cell attachment and spreading directly contact the cultured cells, Cell growth is maintained directly on surfaces of the culture vessel or on supplemental inserts such as cartridges or membranes placed within the vessel, Appropriate attachment and spreading surfaces are produced either by initially selecting a suitable surface material or by subsequently treating an existing surface. Common treatments are well known and include coating surfaces with compositions that promote attachment and spreading. Such compositions are also well known and include polybasic amino acids such as polyornithine and polylysine. Furthermore, the attachment surface may be coated or provided with a known extracellular matrix protein or with compositions or artificial environments that are functionally equivalent to an in vivo extracellular matrix. Such environments enhance serum-free C3A cell growth, maintenance and expression of harvestable bio-products. Typical cell matrix compositions are well known and include laminin, collagen and fibronectin. Other extracellular matrix proteins or artificial extracellular matrix environments, which mimic an in vivo extracellular matrix, are known in the art (see e.g., Synthetic Biodegradable Polymer Scaffolds (Tissue Engineering) A. Atala and D. J. Mooney (Eds.) Birkhauser, 1997).

Upon reaching confluence, the serum-free cells assume an adult phenotype wherein cell division slows dramatically and they develop histologic features of normal human liver cells. Also at confluence, serum-free C3A cells express and synthesize substantial levels of human alpha fetal protein (AFP), human albumin, cc-1-antichymotrypsin, α-1-antitrypsin, antithrombin III, complement C3, Factor V, transferrin and other serum. proteins at reasonably high purity. The term "confluence" as used herein, refers to a density of cultured cells in which the cells contact one another covering most or all of the surfaces available for growth. During pre-confluent growth, selected cells behave like regenerating hepatocytes demonstrating corresponding patterns of regulation of gene expression. Serum-free C3A cells have a rapid doubling time that is substantially less than the doubling time of cells of the parental non-serum-free C3A line. The term "doubling time" as used herein refers to the time it takes for cells in a cell culture to double in number. In a preferred embodiment, the doubling time of the serum-free C3A cell line is in the range of about less than 50% to about less than 70% of the doubling time in serum-free medium of the parental C3A cell line. In a more preferred embodiment, the doubling time of the serum-free C3A cell line is in the range of about less than 60% to about less than 70% of the doubling time in serum-free medium of the parental C3A cell line.

Serum-free C3A cells also exhibit liver specific biological activity, synthesizing serum proteins, isoenzyme, clotting factors and the like. Accordingly, the cells are utilized in serum-free medium as in vitro biological factories that express substantially pure harvestable bio-products including natural-sourced molecules, serum proteins, vaccines and recombinant polypeptides such as antibodies, growth factors, members of the blood cascade, cytokines and morphogenic proteins. Preferably, harvestable bio-products produced by cells of the invention include a single or any combination of a plurality of harvestable polypeptides. More preferably the harvestable polypeptide is selected from the group consisting of: alpha feto protein (AFP), human albumin, α-1-antichymotrypsin, α-1-antitrypsin, antithrombin III, complement C3, Factor V and transferrin. Bio-products expressed by cells of the serum-free C3A cell line are isolated relatively easily during harvesting because of the absence of interfering proteins from the culture medium. Additionally, use of cells of the present invention considerably lessens the risk of cell line or bio-product contamination by organisms or agents commonly found in serum. By the term "harvesting" or "harvestable" is meant culturing cells of the invention in serum-free medium to express a desired bio-product and then recovering or retrieving the bio-product in a substantially pure state from the serum-free culture medium using any retrieval method known in the art (e.g., Culture of Hematopoietic Cells (Culture of Specialized Cells) R. I. Freshney et al., Ed. I. Freshney; Wiley-Liss 1994; Large Scale Cell Culture Technology, B. K. Lydersen Ed., John Wiley & Sons 1993). In one embodiment, the supernatant fluid is recovered from the cell culture and the harvestable bio-products are isolated and purified. In another embodiment, the cells may be grown on a semipermeable membrane or surface that permits diffusion of harvestable bio-products, such as proteins, across the membrane or surface where they are subsequently harvested by isolation and substantial purification. The term "substantially pure" or "substantially purified" as used herein refers to any harvestable bio-product that is substantially free of other proteins, lipids, carbohydrates or other materials with which it is naturally associated.

In one embodiment, a substantially pure harvestable polypeptide from a serum-free C3A cell culture will typically yield a single major band on a non-reducing polyacrylamide gel. The purity of any harvestable polypeptide can also be determined by amino-terminal amino acid sequence analysis. Substantially pure harvestable polypeptides include functional fragments of the polypeptide, so long as its biological activity is retained. Additionally, other recombinant modifications, for example, through site directed mutagenesis of any harvestable polypeptide cDNA, are included. A "recombinant" harvestable polypeptide refers to a harvestable polypeptide produced using any known recombinant molecular biological technique (e.g., cell transfection with an exogenous nucleic acid sequence construct). A "coding sequence of a nucleic acid or a "nucleotide sequence encoding" a particular harvestable polypeptide as used herein, is an endogenous or exogenous nucleic acid sequence that is transcribed and translated into a harvestable polypeptide when placed under the control of an appropriate nucleic acid regulatory sequence.

The invention includes methods using serum-free cells of the invention to express any genetically engineered heterologous eukaryotic nucleic acid sequence encoding a harvestable polypeptide or functional fragment thereof by employing any recombinant technique as described above. Methods of expressing heterologous eukaryotic nucleic acid sequences encoding a correspondingly heterologous polypeptide are well known. The term "heterologous nucleic acid" as used herein refers to any regulatory or structural genetic nucleic acid sequence or material that is not indigenous to the serum-free C3A cell of the invention to which it is introduced (e.g., transfected). Nucleic acid sequences include DNA, cDNA and RNA sequences that encode polypeptides or functional fragments thereof in functioning workable arrangement with any known expression vector. The term "expressing" or "expression" as used herein refers to the full use of the information in a nucleic acid sequence via transcription and translation leading to the production of a corresponding polypeptide sequence that is determined by its encoding nucleic acid sequence. Gene expression is controlled at various points in the progression of steps starting with the initiation of transcription and culminating with the synthesis of a functioning polypeptide. Transfection of a heterologous nucleic acid is accomplished by any conventional method, including the use of viral vectors (*Eukaryotic Viral Vectors*, Cold. Spring Harbor Laboratory, Gluzman ed., 1982), recombinant retroviruses, chemical (calcium phosphate co-precipitation), or physical methods including mechanical procedures (e.g., microinjection, projectile transfection) or liposomes. Genetic material (e.g., a nucleic acid sequence) is inserted into a vector by any of a variety of procedures. In general, the nucleic acid sequence is inserted into an appropriate restriction endonuclease site(s). All such procedures and any others are deemed within the scope of the invention and within the competence of any person of ordinary skilled in the art. Examples of such vectors include chromosomal, nonchromosomal and synthetic DNA sequences (e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies). Any other vector may be used, however, as long as it is replicable and functional within cells of the invention.

Other viral vectors contemplated to be utilized to transfer heterologous genetic material into a serum-free C3A cell of the invention include adenovirus, adeno-associated virus, herpes virus, vaccinia, or an RNA virus such as a retrovirus. Examples of retroviral vectors in which a single foreign gene are inserted include, but are not limited to: Moloney murine leukemia virus (MoMuLV), Harvey murine sarcoma virus (HaMuSV), murine mammary tumor virus (IuMIV), gibbon ape leukemia virus (GaLV) and Rous Sarcoma Virus (RSV). A number of additional retroviral vectors can incorporate multiple genes. Of note are human lentiviral-based vectors that demonstrate long term expression of transgenes in liver and muscle cells (Kafri, T. et al., Nature Genetics 17(3):314; 1997; incorporated by reference herein). All of these vectors can transfer or incorporate a gene for a selectable marker so that transfected cells are identified and generated.

Since recombinant retroviruses are defective, they require assistance to produce infectious vector particles. This assistance is provided by using helper cell lines that contain plasmids encoding all of the structural genes of the retrovirus (gag, env, and pol genes) under the control of regulatory sequences within the long terminal repeat (LTR). These plasmids are missing a nucleotide sequence that enables the packaging mechanism to recognize an RNA transcript for encapsidation. Helper cell lines, which have deletions of the packaging signal, include, but are not limited to $\psi 2$, PA317, PA12, CRIP, CRP-4 and CRE, for example. These cell lines produce empty virions, since no genome is packaged, If a retroviral vector is introduced into such cells, in which the packaging signal is intact but the structural genes are replaced by other genes of interest, the vector is packaged and the vector virion produced, Vector virions produced by this method can then be used to infect a cell line to produce large quantities of chimeric retroviral virions.

The cell line of the present invention has the distinct advantage over previously described hepatocyte cell lines in that its cells are well differentiated and culturable in serum-free medium. Consequently, serum-free C3A cells possess constitutive liver-specific biological activity and they maintain it upon reaching confluence. The term "constitutive" as used herein refers to the fact that serum-free C3A cells normally possess liver-specific biological activity without requiring any particular form of induction. The term "liver-specific biological activity" as used herein refers to physiological/biochemical reactions that take place specifically in normal hepatocytes. Cells of the present invention also possess, express and maintain these liver-specific physiological/biochemical reactions. Furthermore, by use of the term "liver-specific biological activity" herein are included the synthesis and secretion of protein and lower molecular weight products seen in normal hepatocytes. Furthermore, the cells of the invention maintain expression of liver-specific biological functions at levels sufficient to support a subject suspected of having a liver condition or in liver failure or suffering from a disorder brought about or exacerbated by compromised liver function.

Normal hepatocytes perform multiple finely-tuned functions critical to liver functioning and organismal homeostasis. Hepatocytes combine pathways for the simultaneous synthesis and breakdown of carbohydrates, lipids, amino acids, proteins, nucleic acids and co-enzymes. Key "liver-specific" biological fictions include: (1) gluconeogenesis; (2) glycogen synthesis, storage and breakdown; (3) synthesis of serum proteins including albumin, hemopexin, ceruloplasmin, the blood clotting factors. (including Factors V, VII, X, prothrombin and fibrinogen), cyl-antitypsin, antithrombin III, and AFP; (4) conjugation of bile acids; (5) conversion of heme to bile pigments; (6) lipoprotein synthesis; (7) vitamin storage and metabolism; (8) cholesterol synthesis; (9) ammonia metabolism, including urea synthesis and glutamine synthesis; (10) amino acid metabolism, including metabolic conversion and re-utilization of aromatic amino acids; and (11) detoxification and drug metabolism.

Given that the liver accounts for 20% of the body's oxygen consumption, cultures using cells of the present invention require adequate oxygenation to maintain high-level liver-specific biological activity. The constant circulation of oxygenated medium fulfills the metabolic needs of the cells (Wofle, D. et al., Eur. J. Biochem. 151:299-303 (1985)). Adequate oxygen supply also stimulates growth and differentiation functions. The critical role of oxygen in liver metabolism is well documented in literature devoted to the isolated perfused rat liver (IPRL), but its role has largely been ignored in the literature: devoted to cell culture. For example, conventional cultures of HepG2/C3 or HepG2/C3A cells are often oxygen- and therefore energy-limited. If additional oxygen carrying capacity is required in culturing or using cells of the invention, the use of red blood cells or dissolved hemoglobin is provided as described for perfused organs (Gores, G. J. et al., Hepatology 6:511-517; 1986).

To determine if serum-free C3A cells are expressing and maintaining proper metabolic liver-specific activity, the metabolic functions of the cells should be tested, including testing their oxygen dependence, their ability to synthesize glucose and urea, their ability to uptake and conjugate bilirubin and their ability to produce clotting factors. Testing is particularly recommended when the serum-free C3A cells are to be used in a bio-artificial liver device.

Dependence upon oxygen is tested by examining the serum-free cells growth rate in culture that is continuously perfused with increasing concentrations of dissolved oxygen (i.e., over ranges of dissolved oxygen from about 4% to about 20%). Preferably. the cellular growth rate is examined either in serum-free medium containing high concentrations of glucose or in serum-free medium that is glucose-free (with lactate and amino acids as the sole carbon source). Other indicators of metabolic activity are total oxygen consumption, energy charge, redox state, and the ratio of glucose to oxygen consumption. Preferably, these tests also should be conducted at differing concentrations of dissolved oxygen as described above.

Since glucose and urea synthesis are the primary means of removing excess amino acids and ammonia from blood, cells of the invention should be tested for their ability to synthesize both, particularly, when the cells of the invention are used to perform liver-specific functions. Methods of testing glucose and urea synthesis are well known (Kershcer et al., in Methods of Enzymatic Analysis, H. U. Bergmyer, ed., Current ed., Verlag Chemie, Weinheim, Vol. VII, pp. 59-67; 1983).

Production of various vitamin K dependent clotting factors, including prothrombin, factors VII, IX and X, as well as antithrombin III are also easily determined using commonly known methods including, among others, methods such as solid phase radioimmunoassay (Kelly et al., In vitro Cell Dev. Biol. 25:217-222 (1987) and methods using commercially obtained antibodies (DAKO, Inc.).

When cells of the invention are grown on a membrane or in a bio-artificial liver device they provide a useful in vitro model for studying all human liver functions including, but not restricted to, whole organ, cellular, metabolic and molecular functioning. The cells are also useful for studies of: (1) metabolism, (2) toxicology of drugs or other pharmacological compositions, (3) enteric disease, (4) liver specific gene expression or gene regulation and (5) gene delivery techniques, (e.g., gene delivery to hepatocytes using an asialoglycoprotein receptor; Wu et al., *Proc. Assoc. Am. Physicians* 107:2 211-7 1995).

The cells of the invention have advantages over other systems, such as that of the isolated perfused rat liver (IPRL). Being a permanent culture, the serum-free cell line permits rigorous long-term experimental studies to be conducted. Monolayer cultures using serum-free cells of the invention are typically maintained for several months and a bio-artificial liver device prepared with these cells functions normally over a prolonged period (e.g., eight weeks), as determined by albumin production and glucose utilization. Furthermore, cartridges containing cultured cells of the invention reflect human liver metabolism more closely than isolated perfused livers from other species. Thus, the clinical effects of various drug, compounds or metabolites are assessed in a particularly effective in vitro model when cells of the invention are used.

For example, in a particular embodiment, studies of cocaine metabolism and toxicology such as the hydrolytic metabolism of cocaine into benzoylecgonine, ecgonine methyl ester, and ecgonine as described by Falk et al., (J. Pharmacol. Toxicol. Methods 33:2 113-20; 1995) and studies of the metabolism of anticancer agents such as crisnatol as described by Patel et al, (Biochem. Pharmacol. 42:2 337-46; 1991) are carried out in such an in vitro model by employing cells of the invention. Additional metabolic, pharmacological or toxicological studies involving other xenobiotic compounds or disease agents are also contemplated and encompassed within the metes and bounds of the present invention.

In another embodiment, serum-free C3A cells of the invention are used for screening metabolic compounds or by-products, by identifying compositions that affect them. This method comprises incubating compositions suspected of affecting liver or hepatocyte function with serum-free C3A cells under conditions sufficient to allow the components to interact then subsequently measuring the effect the suspect composition has on cells of the invention. The occurrence of a biological response is monitored using standard techniques. For example, many biological responses are identified using the level of expression of certain genes in the serum-free C3A cell subsequent to incubation. Such genes can include early response genes such as fos, myc or jun (Greenberg, Met. and Ziff, E. *Nature,* 311:433, 1984; eds. Burck, et al, in Oncogenes, 1988, Springer-Verlag, New York.). Other genes useful for such studies are known. Techniques that measure the effect of such compositions include Northern blot analysis of RNA (transcription), SDS-PAGE analysis of protein (translation), [$H^3$]-thymidine uptake (DNA synthesis) and antibody reactivity (both intracellular and extracellular).

As described above, cells of the present invention express "liver-specific biological activity" including the ability to perform ammonia and amino acid metabolism, detoxification, and polypeptide production, especially of polypeptides such as coagulation factors. Effecting liver-specific functions is particularly important when the present cells are used in a bio-artificial liver device. Such a device is used to treat a subject having or suspected of having a liver condition, liver related disorder or compromised liver function resulting either from disease or trauma (e.g., fulminant hepatic failure (FHF), awaiting liver transplant or following liver rejection and awaiting liver retransplant). The term "treat" or "treatment," as used herein, comprises administering to the subject a therapeutically effective amount of blood that has been in contact with serum-free cells of the invention for a time sufficient to cleanse the blood before returning it to the subject. The term "cleanse" or "clean," as used herein, means removal of unwanted or undesired molecules from the subject's blood. Moreover, the term "cleanse" or "clean" further includes the release of desired molecules from cells of the invention into the blood before returning it to the subject. The term "therapeutically effective" as used herein, includes the ability to ameliorate the effects of a liver disorder or compromised liver function in a subject responsive to treatment using cells of the invention. The term "ameliorate" as used herein, refers to a lessening of the condition of the responsive subject. The subject of the treatment is preferably a human, however, it is envisioned that any animal with a liver disorder, liver condition or compromised liver function is treated using serum-free C3A cells.

Fulminant hepatic failure is a severe hepatocellular dysfunction generally caused by viral hepatitis, drug reactions or poisoning in which encephalopathy typically occurs within eight weeks of the onset of symptoms (Bemau, J. et al., Sem. Liv. Dis. 6:97-106 (1986); Yanda, R. J. West. J. Med. 149: 586-591 (1988); Katelaris, P. H. et al., Med. Clinics N. Amer. 73:955-970 (1989)). Treatment of FHF or other liver condition, involves culturing cells of the invention in a bio-artificial liver device and cleansing the blood of a subject. The levels of liver-specific biological activity effective to treat or ameliorate a subject suffering from FHF, hepatic failure or compromised liver function are those that result in normal or near normal levels of serum proteins, coagulation factors, amino acids, and other metabolites normally produced in or metabolized by the liver. These various molecules and metabolic products and the physiological as well as pathological ranges of their concentrations or levels are well known and are set forth in Braunwald, E. et al., eds., Harrison's Principles of Internal Medicine, Current Ed., McGraw-Hill, New York, N.Y., incorporated by reference: herein.

The liver specific properties of the serum-free C3A cell line make it particularly useful in a bio-artificial liver device by overcoming the problems of other cells used in such devices. Serum-free C3A cells are permanent, able to duplicate vital biological functions of the liver, and well differentiated. When used in a bio-artificial liver device, the cells are capable of expressing liver-specific biological activities at a level effective to support a subject in hepatic failure or compromised liver function for long periods. Thus, the serum-free C3A cells of the present invention provide a method for supporting liver function. This provides sufficient time for liver regeneration to occur, as well as providing a better environment for liver regeneration by removing circulating toxins. Furthermore, in those subjects whose livers fail to regenerate, they are kept alive while awaiting transplantation. The method of using serum-free C3A cells in a bio-artificial liver device also provides a means of allowing subjects to recover after liver failure before transplantation of a first liver. Also, in those subjects who require emergency second transplants, the availability of a bio-artificial liver device allows them to recover before undergoing a second round of major surgery.

When required, serum-free C3A cells are genetically engineered to contain a heterologous nucleic acid sequence (as described herein) whose expression and subsequent functioning would be particularly beneficial to a subject having a liver disorder or suffering from compromised liver function. Membranes or capillaries of a bio-artificial liver device permit cleansing of blood by permitting the crossover of toxic solutes from blood to cells cultured in the device (e.g., dissolved molecular species such as bilirubin diffuse through the membrane and are taken up and metabolized) as well as permitting the diffusion of vital metabolites from cells cultured in the device to blood returning to the subject undergoing treatment. The selectively permeable or semi-permeable character of the membrane of a bio-artificial liver device also provides a mechanical barrier to components of the immune system from the blood of a subject using the device. Typically, the membrane or capillary features a molecular weight cutoff from about 20,000 daltons up to about 80,000 daltons, generally about 30,000 daltons to about 50,000 daltons. In a preferred embodiment, however, the membrane has pores from about 0.1 $\mu M$ to about 0.3 $\mu m$ in diameter, typically about 0.2 $\mu m$. A pore size diameter in this range excludes cellular elements while permitting proteins and protein complexes to pass through, thus ameliorating serum protein deficiencies of a subject suffering from a liver condition.

Such devices, their methods, use and mechanisms of action are commonly known to a person of ordinary skill in the art. Any such device—several designs of which are discussed in the literature—that is capable of culturing living cells is contemplated to be used with cells of the invention. For example, bio-artificial liver devices are described by Viles et al., (U.S. Pat. Nos. 4,675,002 and 4,853,324); Jauregin, (GB 2,221, 857A); Wolf er al., (International J. of Artificial Organs 2:97-103; 1979); Wolf et al., International J. of Artificial Organs (1:45-51; 1978); and Ehrlich et al., (In vitro 14:443-450; 1978) all of which are incorporated herein by reference. In a preferred embodiment, the bio-artificial liver device includes a hollow fiber cartridge or similar perfusion apparatus having a membrane or capillary as discussed above.

In another embodiment, a bioreactor, such as a hollow fiber bioreactor, can also be utilized as a bio-artificial liver device by permitting cells of the invention to function as a perfused liver. Bioreactors, which employ cartridges or other similar perfusion devices capable of culturing high cell numbers, can replace liver-specific biological activity or allow the accurate assessment of human liver metabolism (as discussed above). Hollow fiber cartridges are two-chamber units that reproduce the three-dimensional characteristics of normal organs (Knazek, R. H., Feder. Proc. 33:1978-1981 (1974); Ku, K. et al., Biotechnol. Bioeng. 23:79-95 (1983) incorporated by reference herein). Culture or growth medium is circulated through the capillary space and cells of the invention—grown in the extracapillary space after seeding—are supplied with a constant inflow of fresh medium (Tharakan, J. P. et al., Biotechnol. Bioeng. 28:1605-1611 (1986). Typically, 1400 cm2 cartridges are inoculated with an effective number of cells (e.g., approximately, $1 \times 10^9$ cells) and grown to confluence in about 14 to about 21 days. Such hollow fiber culture systems are well known (e.g., Heifetz et al., BioTechniques 7:192-199, 1989; Donofrio, D., Amer. Biotech. Lab. September 1989, Publication #940; incorporated by reference herein) and available commercially (e.g., the Anchomet series).

Hollow fiber based systems when used in a bio-artificial liver device offer several advantages. Cartridges support the growth of very high density cultures. Based on the extracapillary volume, 15 to 20 g of cells are grown in a 1400 cm2 unit and 100 g of cells are grown in a 7000 cm2 unit. This amount of cell mass is capable of providing liver support to a subject suffering from liver failure. Also, cartridge-grown cells are polarized and their growth approximates normal liver structure. The cells receive nutrients from the capillary space and secrete waste products into the extracapillary space. The extracapillary space is perfused to prevent the accumulation of toxic products. The continual flow of media and the in-line oxygenator provide a more constant supply of oxygen and energy.

For the most part, the bio-artificial liver devices contemplated to be used with the cells of the invention primarily process blood by attaching to a subject outside the body (e.g., typically, making fluid communication from the device to the subject's blood supply usually between an artery and a vein). Such an arrangement is particularly useful for providing temporary liver support for subjects suffering from a liver disorder [e.g., FHF). Alternatively, the cell line is used within the body as a bio-artificial liver or as a bio-artificial liver support. When used in this manner, cells of the invention are encapsulated or grown in hollow fiber capillary membranes for internal use. Typically, the cells attach to the support upon growth. Linkage materials, however, may be provided to attach the cells to a support (GB 2,221,857A). Cells of the invention are encapsulated in biomaterial such as alginate-polylysine membranes, as taught by Cai et al., (Artificial Organs 12:388-393); Sun et al, (Trans. Am. Soc. Artif. Intern. Organs Vol. XXXII:39-41; 1986); O'Shea et al., (Biochimica Biophysica Acta 804:133-136; 1984); Sun et al., (J. Controlled Release 2:137-141; 1985) and U.S. Pat. No. 4,391,909, all of which are incorporated herein by reference. The encapsulated cells and vehicle capsules are then injected intra-peritoneally into the subject.

Additionally, cells of the invention can be used in a synthetic liver-like tissue comprising fibroblasts and C3a hepatocytes of invention. Typically, co-culture of fibroblasts and hepatocytes do not automatically adopt the arrange typically found in the liver; and because the two cell types then communicate poorly, the hepatocytes are often functionally inefficient. However, Toner et al., (Fall Meeting of the Materials Research Association, 1-5 Dec. 1997; Nature, 39: 128; 1988) describe imprinting a substrate (e.g., borosilicate wafer) using standard photolithographic techniques of microelectronic technology with patterned films of collage, which promotes cell adhesion. Hepatocytes of the invention can then be cultured on such surfaces, adhering only to the collagen-coated regions. Fibroblasts are then introduced on the bare surface regions producing an intimate mixture of the two cell types in a periodic pattern allowing any ratio of cell types on the substrate permitting adjustment to any physiological value. Using this technique any pattern size, shape, and number density can be deduced and engineered to order in such an artificial liver tissue.

Without further elaboration, it is believed that a person of ordinary skill in the art can, using the preceding description, utilize the present invention to its fullest extent. The following examples are put forth solely for the purpose of illustration as to make and use the cells or cell lines of the present invention, and are not intended, nor should they be construed, to limit the scope of what the inventors regard as their invention. Unless indicated otherwise below, parts are parts by weight, molecular weight is weight average molecular weight, temperature is in degrees Centigrade, and pressure is at or near atmospheric.

EXAMPLE 1

Generation of a Serum-Free C3A Clone

Seven commercial serum-free formulations, and one custom serum-free formulation (Hepatix Inc.), were tested for the ability to support the consistent growth of C3A cells during passaging to serum independent status:
(1) JRM Biosciences' ExCell 620 medium (product #14620-79P) supplemented with 2 nM L-glutamine;
(2) Gibco's Hepatozyme-SFM (catalog #17705-021) supplemented with L-glutamine;
(3) Gibco's Aim V Medium (catalog #12055-091);
(4) HyClone's HyQ-CCM4 medium (catalog #SH30106.02);
(5) Irvine Scientific's IS293 medium (catalog #99269);
(6) Clonetics' Hepatocyte Maintenance Medium (catalog #CC-3197) supplemented with insulin and dexamethasone;
(7) BioWhittaker prototype Hepatocyte Medium (ref~97-0454) supplemented with glucagon, insulin, dexamethasone, sodium selenite, triiodothyronine (T3) and linoleic acid/bovine serum albumin (Hepatix supplements); and
(8) a Hepatix serum-free medium formulation consisting of 25% Waymouth MAB 87/3 medium (Gibco catalog #86-5124EL) and 75% Minimum Essential Medium (Gibco catalog #41500-018), supplemented with glucagon, insulin, dexamethasone, sodium selenite, triiodothyronine and linoleic acid/bovine serum albumin.

A confluent flask of C3A cells was trypsinized, then neutralized by adding complete serum-containing (5% bovine calf serum) medium (Hepatix Inc. MM medium from HyClone, catalog #SH3A323.01). The cells were subsequently aliquotted into 5×106 viable cell aliquots and re-centrifuged (1000 rpm) for 5 minutes at 25° C. Each pellet generated by the procedure was resuspended in a 50:50 mixture of serum-containing Hepatix MM medium and one of the eight serum-free mediums listed above. Cell cultures were grown and maintained for one-week (three equally-spaced feedings) with the appropriate corresponding 50:50 medium mixture.

At confluence, the cells were re-trypsinized. divided (1:8 ratio), and transferred into culture medium as described except that the serum-containing portion of the medium was reduced (e.g., from 50% to a 25:75; serum-containing: serum-free mixture). Cells were fed and maintained as above.

During the third cell passage in mixed serum-containing and serum-free medium, cells from each culture were harvested and transferred into a serum-free medium (one of the eight serum-free mediums listed above). Cells were passaged four times under culture conditions described above. Cells in Gibco's Hepatozyme-SFM and HyClone's HyQ-CCM4 serum-free medium (Nos. 2 and 4) exhibited a rounded-up appearance which was attributed to a loss of surface adherence.

EXAMPLE 2

Comparative Growth Rates of C3A Clone in Different Serum-Free Media

After four passages in 100% serum-free medium, a comparative growth rate analysis was performed on cells from each of the eight cultures. Growth rate was assessed using the Promega MTS assay system in medium Nos. 1, 3 and 5 (respectively, JRH Biosciences' ExCell 620 supplemented with 2 mM L-glutamine; Gibco's Aim V; and Irvine Scientific's IS293). The most consistent growth was determined to be for cells maintained in medium No. 1 (JRH Biosciences' ExCell 620). Consequently, this medium was subsequently employed to produce clonal isolates of serum-free cells.

EXAMPLE 3

Generation of C3A Clonal Cell Colonies

Clones were generated by limiting dilution (2.5 cells per well in JRH Biosciences' ExCell 620 serum-free medium (JRH-SFM)) in a 96-well plate. Using this strategy, twelve separate clones were initiated, harvested, expanded and subsequently cryo-preserved. Of the twelve clonal isolates, one clone (designated 2.5B1) was chosen for further development.

The 2.5B1 clone at passage zero (P0) was harvested 21 days after plating. It was re-plated (96-well tissue culture plate) for 4 days (PI), trypsinized and seeded into a T25 flask (P2) for expansion in JRH-SFM (No. 1). Twelve days later it was harvested, re-plated into another T25 flask (P3) for 2 days, subsequently split (1:3) into a T75 flask (P4), then split (1:8) approximately every seven days with thrice weekly feedings of JRH-SFM. The 2.5B1 clonal culture was successfully passaged 14 times with over 30 population doublings since P2.

EXAMPLE 4

Characterization of C3A Clonal Cell Colonies

One characterization of the serum-free 2.5B1 clonal colony measured the secretion rates of two human proteins (i.e., human alphafetoprotein (AFP) and human albumin) which are expressed in cells of the clone. The results of the measurement are illustrated in Table 1. The data demonstrate that approximately $27.5 \times 10^6$ cells. generated from the 2.5B1 clone, produce an average of 390 µg of albumin and 96 µg of AFP in a 24-hour period (n=6).

TABLE 1

| PASSAGE NUMBER | TOTAL CELLS HARVESTED (X10E6) | DAYS IN CULTURE | TOTAL POPULATION DOUBLINGS SINCE P2 | % VIABILITY (TRYPAN BLUE) | TOTAL ALBUMIN (µg) | TOTAL AFCP (µg) |
|---|---|---|---|---|---|---|
| P4 | 40.10 | 6 | 2.85 | 95 | 485 | 120 |
| P5 | 26.08 | 7 | 5.15 | 95 | 342 | 69 |
| P6 | 17.58 | 7 | 7.65 | 87 | 389 | 98 |
| P7 | 29.00 | 7 | 11.16 | 95 | 416 | 103 |
| P9 | 23.28 | 7 | 16.98 | 96 | 395 | 90 |
| P10 | 28.96 | 7 | 20.35 | 95 | 310 | 93 |
| AVG | 27.50 | 7 | — | 94 | 390 | 96 |

Figure 1F:
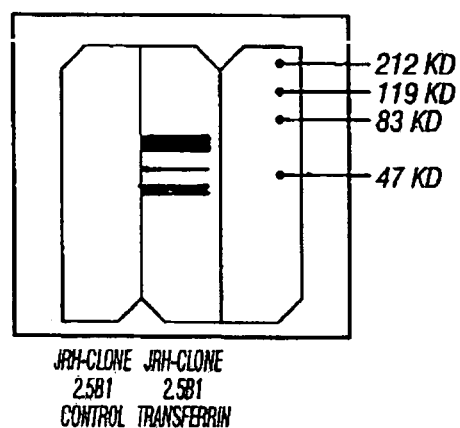

Further characterization of protein expression from these cells using Western Blot techniques demonstrated that at passage 11 (PI 1) these serum-free C3A cells also express the following harvestable polypeptides: (1) alpha-1-antichymotrypsin, (2) alpha-1-antitrypsin, (3) antithrombin III, (4) complement C3, (5) Factor V and (6) transferrin (FIG. 1; Western blot with 10% SDS-PAGE gels).

EXAMPLE 5

Figure 2:
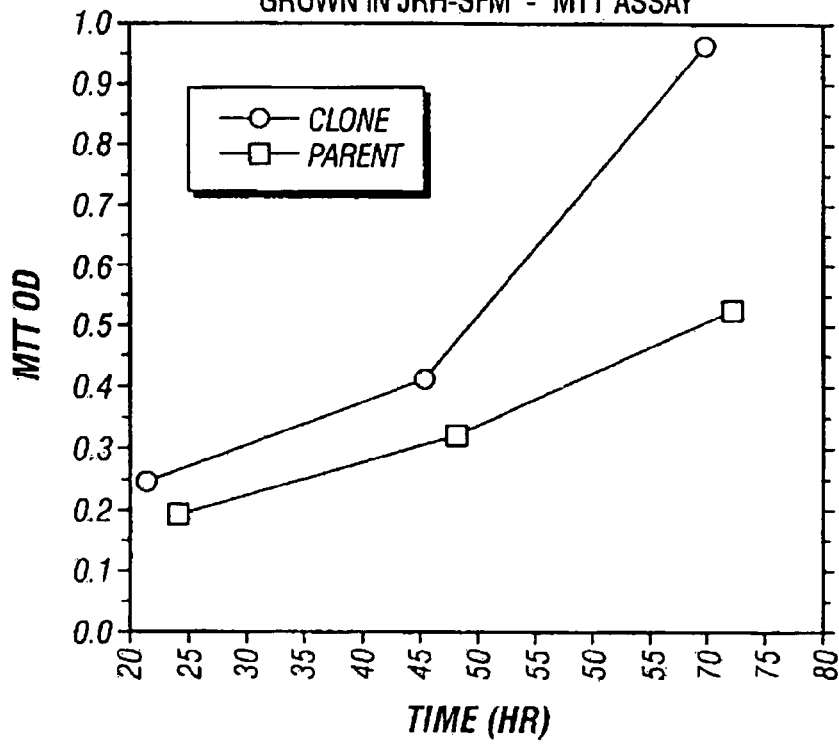
FIG. 2 is graph illustrating the comparative growth rates of serum-free C3A cells and cells of the parental C3A cell line.

Comparison of Serum-Free C3A Clonal Cell Growth Rate with Parental C3A Cell Growth Rate To determine if passaging and clonal derivation of the C3A parental cells to serum independence compromised their viability or their capability for growth and maintenance, the growth rate of the 2.5B1 serum-free cells was compared to the growth rate of cells from the parental C3A line using JRH-SFM medium. The results (FIG. 2) demonstrate that serum-free 2.5B1 cells have a higher growth rate and a significantly shorter doubling time than the parental C3A cells. The data indicate a doubling time of approximately 24 hours for cells of the 2.5B1 clone while the doubling time for cells from the parental C3A cell line was approximately 35 hours. Thus, the doubling time of the cells of the invention in serum-free medium is less than about 70% of the doubling time in serum-free medium of cells from the corresponding C3A cell line

EXAMPLE 6

Serum-Free C3A Cell Clone Colonies Exhibit a Normal Growth Profile

The normality and viability of the serum-free 2.5B1 clone was demonstrated by examining its growth profile. Cells from the 2.5B clone were seeded onto an Althin cartridge (Unisyn CP-3000) as described above and grown for nine days. The results (Table 2) indicate a normal growth and metabolic profile.

TABLE 2

| DATE OF SAMPLE | ALBUMIN PRODUCTION [MG/DAY] | GLUCOSE CONSUMPTION [GM/DAY] |
|---|---|---|
| Day 1 | 3.2 | 0.3 |
| Day 2 | 17 | 0.96 |
| Day 3 | 41 | 2.3 |
| Day 4 | 92 | 4.1 |
| Day 5 | 172 | 7.1 |
| Day 6 | 256 | 9.0 |
| Day 7 | 540 | 12.4 |
| Day 8 | 600 | 14.0 |
| Day 9 | 602 | 15.0 |

EXAMPLE 7

Determination of Metabolism Un Serum-Free C3A Cell Colonies

To assess the feasibility of using the serum-free C3A cells (2.5B clone) as surrogate hepatocytes, several critical requisite metabolic processes are easily determined. Experiments can measure whether the cells metabolize aerobically or anaerobically under standard cell culture conditions.

Initial determinations measure glucose utilization in simple monolayers to determine glucose concentration (e.g., over a 24 hour period). Glucose utilization is examined either under standard conditions or in pre-oxygenated media. To determine if excess glucose utilization is due to failure of the cells to shunt pyruvate through the citric acid cycle, similar experiments are performed in the presence of nitropropionic acid (NOP). NOP is a transition state analog of succinate that irreversibly inactivates succinate dehydrogenase, preventing utilization of the citric acid cycle (Alston, T. A. et al., Proc. Natl. Acad. Sci. U.S.A. 74:3767-3771 (1977)). The addition of NOP is ineffective under hypoxic conditions since the citric acid cycle is not active. In oxygenated cultures, however, NOP shifts the glucose utilization curve to resemble a hypoxic curve. A crucial variable in assessing the cells metabolic activity is to ensure that the metabolic pathway is not oxygen limited, and therefore energy limited. The extent to which cultured cells may be oxygen limited is not widely appreciated. The synthesis of glucose and urea from lactate are tested in T-flasks in the absence of added oxygen.

EXAMPLE 8

Determination of Gluconeogenesis Activity in Serum-Free C3A Cells**

Glucose synthesis from lactate or amino acids is a major liver-specific metabolic function. Oleic acid stimulates glucose production since fatty acids supplies energy for the process while lactate supplies the carbon. Glucose synthesis rates are measured to determine if the rate of glucose synthesis in serum-free C3A cells is similar to the rate of glucose synthesis in perfused rat liver or isolated rate hepatocytes (Krebs, H. A., et. al., pp. 269-291 (1976)). Determination of this rate is a measure of energy flux through an entire liver-specific pathway, not simply a measurement at the level of a single enzyme. Such a measure indicates if critical gluconeogenic enzymes, pyruvate carboxylase, phosphoenolpyruvate carboxy-kinase and fructose diphosphatase are adequately expressed and appropriately regulated in serum-free C3A cells.

** Experiments reported in the remaining examples are performed in airtight vessels having an atmosphere of 95%0;+5% CO, containing serum free medium gassed with this same atmospheric mixture.

EXAMPLE 9

Determination of Glycogen Synthesis Using Serum-Free C3A Cells

Newgard, et al., (Biol. Chem. 258:8046-8052 (1983)) used a double labeling technique, quantitating the percentage of the administered glucose which passed first through the glycolytic pathway before deposition as glycogen, to demonstrate that glucose administration to starved rats resulted first in degradation to pyruvate then subsequently in re-synthesis to glycogen not, as expected, in direct re-synthesis to glycogen. Given these findings, a continuing question exists as to the location of the initial site of glucose metabolism under such conditions (glucose may be utilized first by a peripheral tissue such as muscle then sent back to the liver as lactate to be synthesized into glucose-6-phosphate and glycogen or, alternatively, glucose might be differentially utilized by different metabolic zones within the liver).

To determine the location of the initial site of glucose metabolism under such conditions, similar double labeling studies to those of Newgard, et al., can be performed using serum-free C3A cells of the invention. Such studies demonstrate if the liver is capable of performing all of these metabolic interconversions. When $C^{14}$-glucose and $H^3$-water is simultaneously administered with a large amount of unlabeled sugar, the majority of the glucose can first be degraded first through glycolysis and then re-synthesized to glycogen, indicated by the amount of $H^3$ found in the glycogen. Glucose. that is passed through glycolysis then re-synthesized, will have much more $H^3$ incorporated than glucose that is directly utilized. When labeled glucose and $H^3$-water are administered for varying lengths of time after the initial bolus of glucose, diminishing amounts of the carbohydrate are passed through glycolysis before deposition in glycogen, indicated by a declining amount of $H^3$ relative to $C^{14}$. Such results would indicate that glycolysis and gluconeogenesis are active simultaneously but. with the addition of glucose, there is a gradual switch to direct glycogen synthesis.

EXAMPLE 10

Determination of Nitrogen Metabolism Using Serum-Free C3A Cells

The liver is the major organ for clearance of ammonia and other nitrogen containing compounds, and nitrogen imbalance is one of the more serious metabolic problems faced by a subject suffering from a liver disorder. Therefore, the ability of serum-free C3A cells to perform liver functions is determined by measuring their ability to synthesize urea from lactate and ammonium chloride. The resulting rate of urea synthesis is compared with rates established measurements using perfused rat livers and isolated hepatocytes (Krebs, H. A. et al., pp. 269-291 (1976)).

One test of nitrogen metabolism incubates serum-free C3A cells with a serum sample from a patient suffering from a liver disorder (e.g., FHF). HeLa or HepaSK cells can then be used as a control for the ability to metabolize nitrogen compounds. FHF serum typically contains elevated levels of ammonia and amino acids, notably phenylalanine and ornithine. Treatment of this serum with 0.5 g of serum-free C3A cells for 3 hours measures the ability to restore ammonia to below normal levels, increase urea and reduce levels of amino acids. Phenylalanine degradation (through tyrosine under the action of phenylalanine hydroxylase), can decline dramatically under such treatment. Phenylalanine hydroxylase is dependent on tetrahydrobiopterin reductase to supply coenzyme for the reaction.

This test also measures flux through a liver specific pathway by indicating serum-free C3A cells can achieve normal hepatocyte metabolism.

EXAMPLE 11

Determination of Serum-Free C3A Cells Growth in Hollow Fiber Cartridges

Hollow fiber devices for cell culture have been used primarily for the growth of hybridomas in the production of monoclonal antibodies (Heifetz, A. H. et al., Bio Techniques 7:192-199 (1989)). Since these devices are equipped with an in-line oxygenation system, it is expected that serum-free C3A cells will perform better when grown in the hollow fiber device (e.g., an Amicon FloPath 1400 cartridge) than in static culture. Hollow fiber devices have an additional advantage of mimicking the three dimensional architecture of the normal liver.

Glucose utilization and albumin production are monitored daily. The cartridge is inoculated with approximately $1 \times 10^9$ cells. Since no method currently exists to accurately assess the number of cells resident in a cartridge after albumin production levels off while maintaining the culture, an estimate must be made (By assuming that the extra capillary space of the device is fully occupied (~20 ml), the maximum number of cells is calculated at approximately 20×10⁹, or 20 g by weight.).

Under normal culture conditions in T-flasks or multi well dishes (which may be oxygen limited as discussed above) serum-free C3A cells can produce about 390 μg of albumin/24 hour in a confluent culture. Serum-free C3A cells grown in a hollow fiber cartridge as described above may exceed this amount. The predicted increase in yield of albumin is attributed to physiologic culture conditions more liver-like using a hollow fiber device.

EXAMPLE 12

An Animal Model for the Treatment of a Subject having a Liver Disorder or Compromised Liver Function using Serum-Free C3A Cells in a Bio-Artificial Liver Device Serum-free C3A cells can be used in an animal model predictive of human subjects treated for a liver disorder or condition using similar methodology. The serum-free cells are grown to high densities in hollow fiber cartridges or other bioartificial liver device, as described above. This permits the cells to function similarly to a perfused human liver. A bio-artificial liver device, prepared in this manner using methods described herein, is used in experiments that mimic subjects suffering from a serious liver disorder (e.g., FHF). Liver disorders are modeled in animals injected with a sub-lethal dose of acetaminophen and the parameters of liver function are monitored throughout the treatment regime.

Under sterile conditions and general anesthesia, a shunt is created between the carotid artery and the internal jugular vein in an animal (e.g., a dog). An incision is made along the anterior border of the sternocleidomastoid and the carotid artery and internal jugular vein are exposed. Both vessels are ligated at the level of mandibular angle, and a shunt is fashioned between the two vessels. Silastic dialysis catheters are sutured in place, brought out through the incision and the wound is closed with 4/0 silk. The animals are observed until recovery from anesthesia and subsequently examined six hours later. Distress is monitored and acetaminophen (100 mg/kg) is administered at 6 hours per need. The sutures are removed after one week and dialysis is not started until the shunt has matured. Attachment of a bio-artificial liver device is performed by attaching the cartridge to the afferent and efferent limbs of the shunt via dialysis catheters. The wound remains covered by surgical tape at all times to avoid injury to the shunt site. Injections of acetaminophen (750 mg/k for the first dose, 200 mg/k for the second two) are accompanied by a subcutaneous injection of 1% xylocaine to avoid a painful local reaction. Liver impairment in the group receiving a sub-lethal dose does not cause serious symptoms, while the group receiving the lethal dose experiences anorexia, vomiting and diarrhea in the pre-comatose state. According to the model of Francavilla, A. et al., (Gastroenterology 96:470-478; 1989) additional drugs are not administered to the control animals (animals receiving liver dialysis are asymptomatic). A bio-artificial liver device containing cultured cells of the invention is then used to remove toxins, conjugate bilirubin, restore a normal amino acid profile and replace serum proteins and clotting factors. Such treatment prevents the death of the animal.

The bio-artificial liver device is also used to support liver functions in an hepatic dogs given a lethal dose of acetaminophen. The dogs are kept alive by intermittent extracorporeal liver dialysis.

The foregoing written specification is considered to be sufficient to enable a person of ordinary skill in the art to practice the invention. The present invention is not to be limited in scope by the cell line deposited, since the deposited embodiment is intended as a single illustration of one aspect of the invention and any cell lines that are functionally equivalent are within the scope of this invention. The deposit of material does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent from the foregoing description and fall within the scope of the appended claims.

What is claimed is:

1. A method of producing a serum-free C3A clonal cell line deposited as ATCC accession No. CRL-12461, wherein cells of the clonal cell line have a doubling time in serum-free medium of less than 70% of the doubling time in serum-free medium of a parental C3A cell line and maintain liver-specific biological activity, and wherein cells of the clonal cell line express alpha fetal protein, albumin, α-1-antichymotrypsin, α-1-antitrypsin, antithrombin III, complement C3, Factor V and transferrin, comprising:
   a) sequentially culturing cells of a parental C3A cell line deposited as ATCC accession No. SD 2078 or SD 3283, in a series of medium having incrementally decreasing concentration of serum, the final medium in the series being serum free,
   b) generating a clonal cell colony of the cells from the final medium in the series of a) in serum-free medium; and
   c) propagating the clonal cell colony in serum-free medium, thereby producing the serum-free C3A clonal cell line.

2. The method of claim 1, wherein one of the series of medium having incrementally decreasing concentration of serum in the sequential cultures series has a ratio of serum containing and serum-free medium of about 50:50.

3. The method of claim 1, wherein one of the series of medium having incrementally decreasing concentration of serum in the sequential cultures series has a ratio of serum containing and serum-free medium of about 25:75.

4. The method of claim 1, wherein the serum-free medium is supplemented with 2 mM L-glutamine.

5. The method of claim 1, wherein the liver-specific biological activity is selected from the group consisting of
   a) gluconeogenesis activity;
   b) glycogen synthesis, storage and breakdown activity;
   c) synthesis of serum proteins;
   d) conjugation of bile acids;
   e) conversion of heme to bile pigments;
   f) lipoprotein synthesis activity;
   g) vitamin storage and metabolism activity;
   h) cholesterol synthesis activity;
   i) ammonia metabolism activity;
   j) amino acid metabolism activity;
   k) detoxification and drug metabolism activity; and
   l) any combination of (a) to (k).

6. The method of claim 1, wherein the liver-specific biological activity maintained by cells of the clonal cell line is equivalent to that of the parental C3A cell line.

7. The method of claim 1, wherein cells of the clonal cell line have a doubling time in serum-free medium of less than 60% of the doubling time in serum-free medium of the parental C3A cell line.

* * * * *